(12) United States Patent
Fukuoka

(10) Patent No.: US 11,406,668 B2
(45) Date of Patent: Aug. 9, 2022

(54) PHARMACEUTICAL COMPOSITION FOR USE IN IMPROVING QUALITY OF SCALP OR SKIN, WOUND HEALING, OR IMPROVING QUALITY OF HAIR

(71) Applicant: Hirotaro Fukuoka, Tokyo (JP)

(72) Inventor: Hirotaro Fukuoka, Tokyo (JP)

( * ) Notice: Subject to any disclaimer, the term of this patent is extended or adjusted under 35 U.S.C. 154(b) by 21 days.

(21) Appl. No.: 16/610,638

(22) PCT Filed: Oct. 2, 2017

(86) PCT No.: PCT/JP2017/035876
§ 371 (c)(1),
(2) Date: Nov. 4, 2019

(87) PCT Pub. No.: WO2019/069354
PCT Pub. Date: Apr. 11, 2019

(65) Prior Publication Data
US 2020/0101114 A1 Apr. 2, 2020

(51) Int. Cl.
*A61K 35/28* (2015.01)
*A61P 17/02* (2006.01)
*A61K 9/08* (2006.01)
*A61Q 7/00* (2006.01)

(52) U.S. Cl.
CPC .............. *A61K 35/28* (2013.01); *A61K 9/08* (2013.01); *A61P 17/02* (2018.01); *A61Q 7/00* (2013.01)

(58) Field of Classification Search
None
See application file for complete search history.

(56) References Cited

U.S. PATENT DOCUMENTS

| | | | |
|---|---|---|---|
| 2014/0234272 A1* | 8/2014 | Vesey | A61P 37/00 424/93.7 |
| 2016/0000698 A1 | 1/2016 | Yang et al. | |
| 2016/0000699 A1 | 1/2016 | Yang et al. | |

FOREIGN PATENT DOCUMENTS

| | | |
|---|---|---|
| CN | 106318904 A | 1/2017 |
| CN | 106659741 A | 5/2017 |
| EP | 3 111 946 A1 | 1/2017 |
| JP | 2017/521363 * | 8/2017 |
| JP | 2017-521363 A | 8/2017 |
| KR | 20110119061 A | 11/2011 |
| KR | 20150054747 A | 5/2015 |
| KR | 20160060914 A | 5/2016 |
| WO | WO 2012/122604 A1 | 9/2012 |

OTHER PUBLICATIONS

Yang J. et al. Potential Application of Adipose Derived Stem Cells and Their Secretory Factors to Skin. Expert Opinion on Biological Therapy 10(4)495-503, Apr. 2010. (Year: 2010).*

Park, B. et al. Hair Growth Stimulated by Conditioned Medium of Adipose Derived Stem Cells is Enhanced by Hypoxia. Biomedical Research 31(1)27-34 2010. (Year: 2010).*

Fukuoka H. et al. Hair Regeneration Therapy. Current Stem Cell Research & Therapy 12(7)531-534 2017. (Year: 2017).*

International Search Report dated Nov. 28, 2017 in PCT/JP2017/035876 filed on Oct. 2, 2017.

Lee, E. Y. et al., "Hypoxia-enhanced wound-healing function of adipose-derived stem cells: Increase in stem cell proliferation and up-regulation of VEGF and bFGF," Wound Repair and Regeneration, vol. 17, 2009, pp. 540-547.

Fukuoka, H. et al., "3. Method of Treatment Using Cytokines—With Adipose-derived Stem Cells Secreted Protein-," Japanese Journal of Plastic Surgery, vol. 56, 2013, pp. S149-S154, 16 total pages (with English translation).

Fukuoka, H. et al., "Hair Regenerated Therapy with Growth Factors in Adipose-derived Stem Cells Secreted Protein," Japanese Journal of Plastic Surgery, vol. 53, No. 10, 2010, pp. 1095-1104, 32 total pages (with English translation).

Park, B-S. et al., "Hair growth stimulated by conditioned medium of adipose-derived stem cells is enhanced by hypoxia: evidence of increased growth factor secretion," Biomedical Research, vol. 31, No. 1, 2010, pp. 27-34.

Fukuoka, H. et al., "The Latest Advance in Hair Regeneration Therapy Using Proteins Secreted by Adipose-Derived Stem Cells," The American Journal of Cosmetic Surgery, vol. 29, No. 4, 2012, pp. 273-282, 11 total pages.

Moon, K. M. et al., "The Effect of Secretory Factors of Adipose-Derived Stem Cells on Human Keratinocytes," International Journal of Molecular Sciences, vol. 13, 2012, pp. 1239-1257.

Notice of Reasons for Refusal dated Oct. 9, 2018 in Japanese Patent Application No. 2018-544574 (with English translation).

Decision to Grant a Patent dated Feb. 21, 2019 in Japanese Patent Application No. 2018-544574 (with English translation).

Extended European Search Report dated Apr. 22, 2021 in European Patent Application No. 17927917.9, 7 pages.

Festa E. et al., "Adipocyte Lineage Cells Contribute to the Skin Stem Cell Niche to Drive Hair Cycling", vol. 146, Sep. 2, 2011, pp. 761-771.

Driskell R. R. et al., "Defining Dermal Adipose Tissue", Experimental Dermatology, vol. 23, 2014, pp. 629-631.

Satoh T. et al., "Critical Role of Trib1 in Differentiation of Tissue-resident M2-like Macrophages", Nature, vol. 495, Mar. 28, 2013, pp. 524-530.

Schmidt B. A., et al., "Intradermal Adipocytes Mediate Fibroblast Recruitment During Skin Wound Healing", Development, vol. 140, 2013, pp. 1511-1521.

Combined Chinese Office Action and Search Report dated Jun. 2, 2020 in Chinese Patent Application No. 201780089744.7, 9 pages.

Shin, H., et al., "Clinical use of conditioned media of adipose tissue-derived stem cells in female pattern hair loss: a retrospective case series study", International Journal of Dermatology, vol. 54, 2015, pp. 730-735.

(Continued)

*Primary Examiner* — Ralph J Gitomer

(74) *Attorney, Agent, or Firm* — Oblon, McClelland, Maier & Neustadt, L.L.P.

(57) ABSTRACT

The present invention provides a pharmaceutical composition for use in modifying scalp or skin, promoting wound healing, or modifying hair, comprising a secretion from adipose stem cells as an active ingredient, wherein 0.3 to 0.6 μg of the secretion in terms of protein abundance per site in scalp or skin is administered.

6 Claims, 10 Drawing Sheets

(56) References Cited

OTHER PUBLICATIONS

Zhejiang Science and Technology Publishing, Scar Plastic Surgery, Section IV Skin tissue engineering therapy (with English translation), Mar. 31, 2015, p. 514.

Chinese Office Action dated Jun. 17, 2021 in Chinese Patent Application No. 201780089744.7, 5 pages.

"Biochemical Regulation of Hair Follicle Growth" Current Dermatology and Venerology/Wu Zhihua = Ghuangzhou: Guangdong People'sPublishing House, 2000, 9 pages.

The Search Report and Wntten Opinion dated Jun. 10, 2021, in Singapore Application No. 11201911271U.

Hu L et al, "Effects of adipose stem cell-conditioned medium on the migration of vascular endothelial cells, fibroblasts and keratinocytes", Experimental and Therapeutic Medicine 5: 701-706, 2013.

Fukuoka H et al, "Hair Regeneration Treatment Using Adipose-Derived Stem Cell Conditioned Medium: Follow-up With Trichograms", EPlasty, 65-72, 2015.

\* cited by examiner

TIP

ROOT

TREATED SITE UNTREATED SITE

FIG. 2
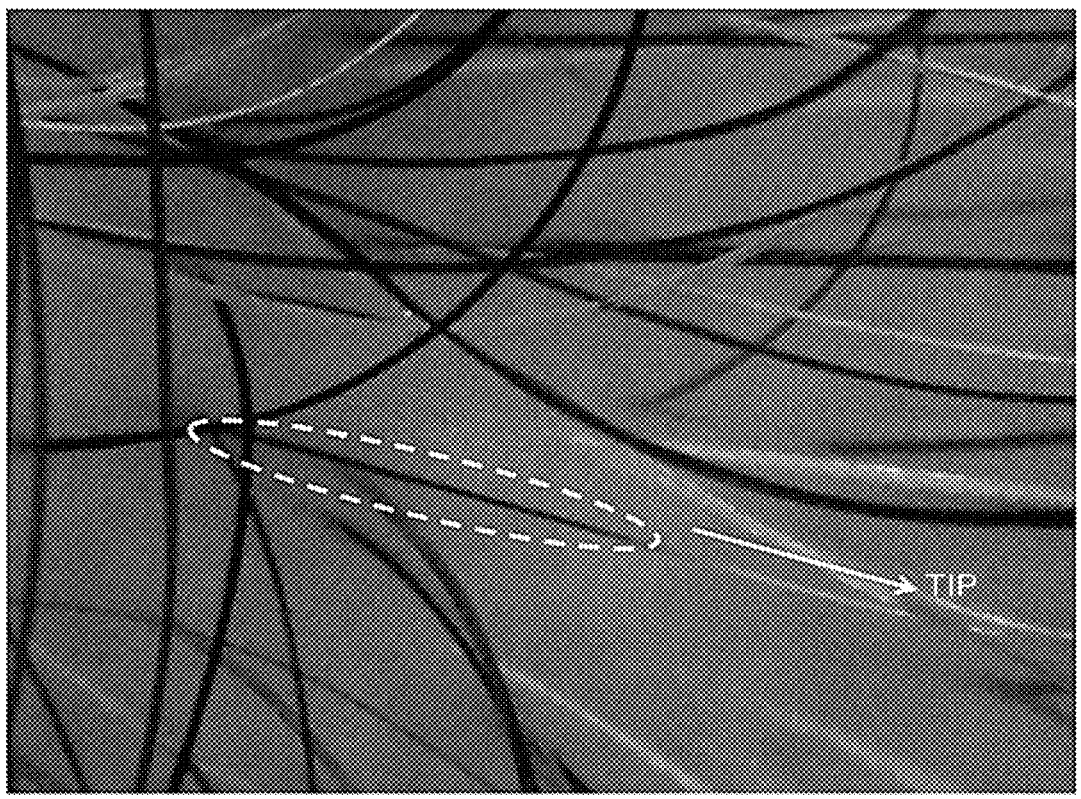
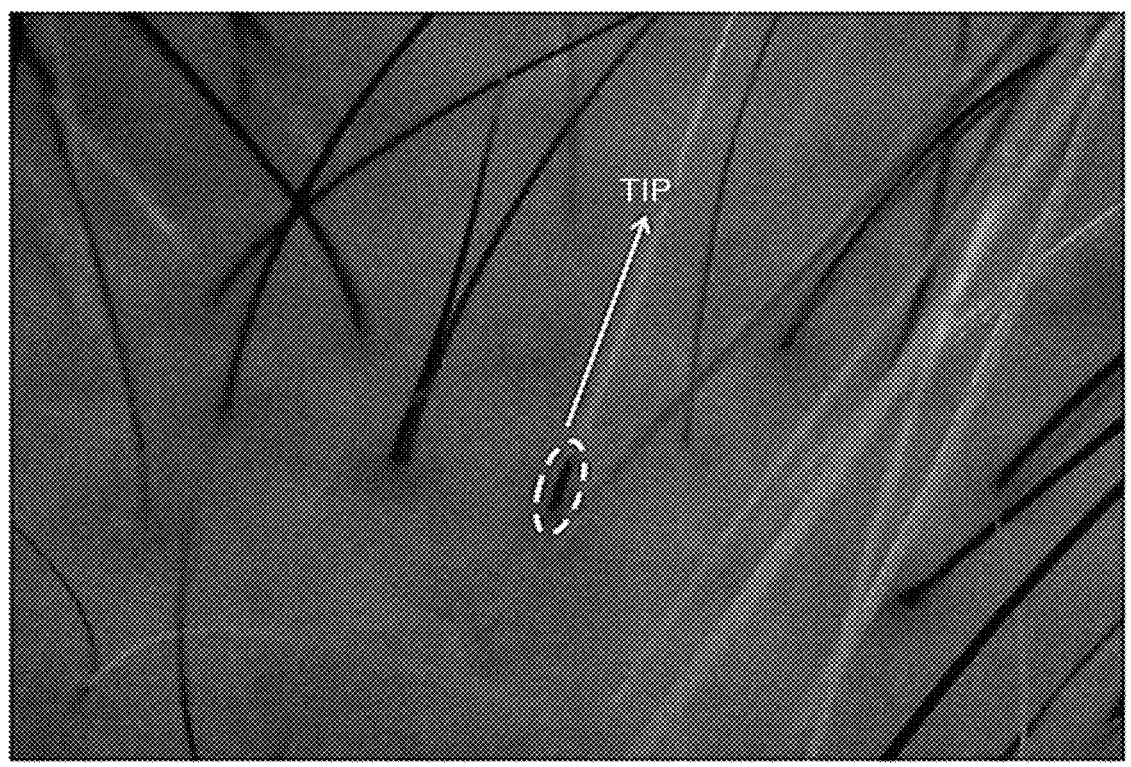

FIG. 3
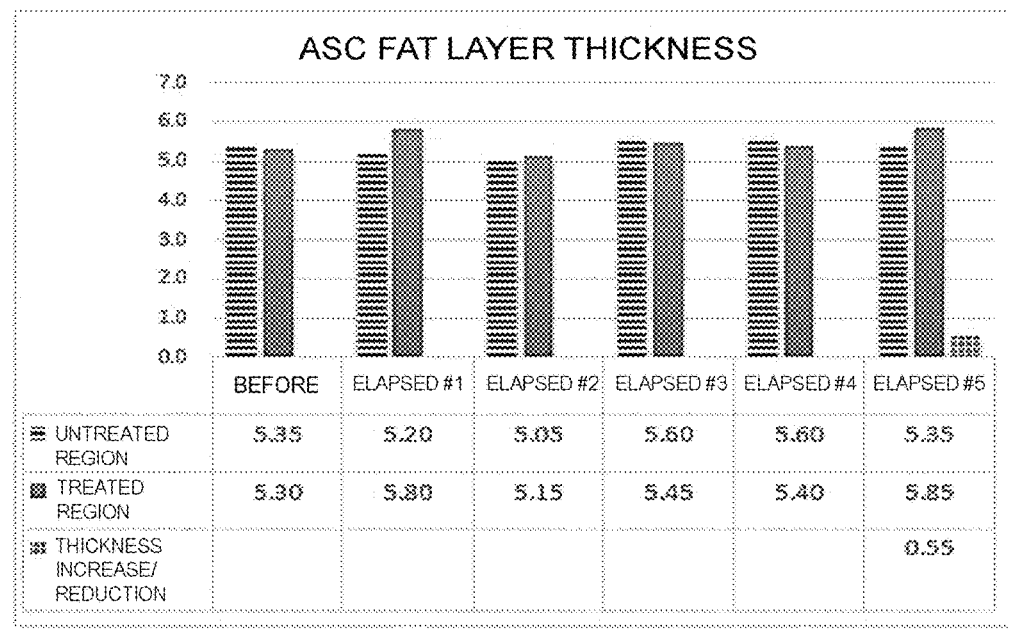
BEFORE TREATMENT
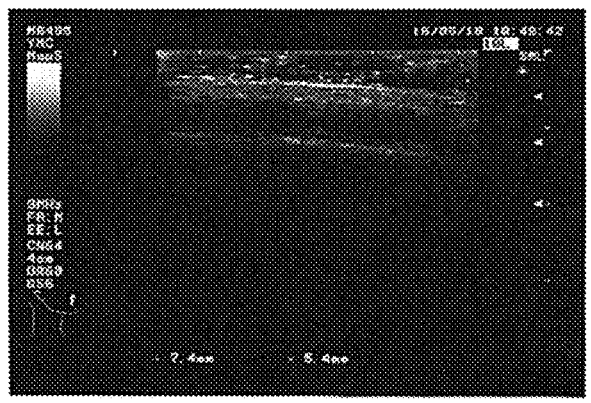
5 MONTHS AFTER TREATMENT
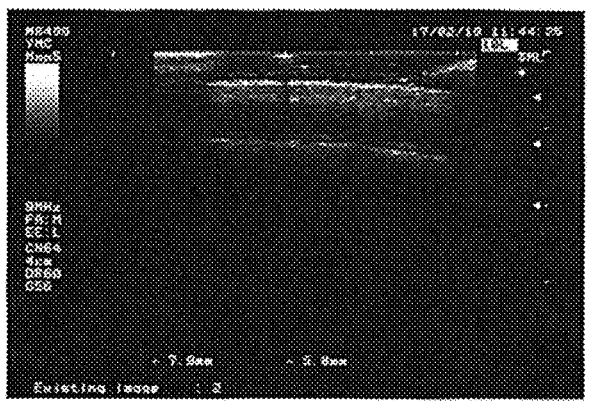

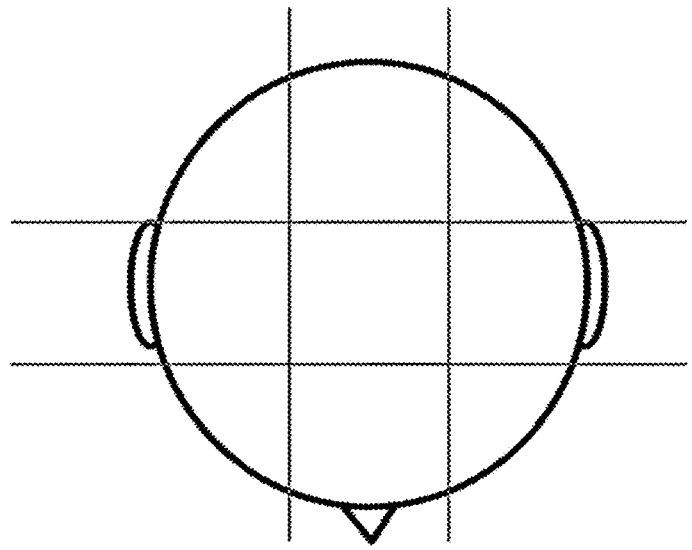

LENGTH MEASUREMENT EXAMPLE (C)

PATIENT C

PHARMACEUTICAL COMPOSITION FOR USE IN IMPROVING QUALITY OF SCALP OR SKIN, WOUND HEALING, OR IMPROVING QUALITY OF HAIR

TECHNICAL FIELD

The present invention relates to a pharmaceutical composition and method for use in improving quality of scalp or skin, wound healing, or improving quality of hair.

BACKGROUND ART

It is disclosed that the adipose-derived stem cell secretion extracted from adipose stem cells has an action stimulating hair matrix cells and a hair increasing effect (Non Patent Literature 1). In addition, hair increasing agents by suppressing male hormone have also been developed. However, although these treatments have a hair increasing effect during the treatment period, the hair increasing effect disappears when the treatment is ended.

CITATION LIST

Non Patent Literature

[Non Patent Literature 1] Byung-Soon Park et al., Biomedical Research, 31(1): 27-34, 2010

SUMMARY OF INVENTION

The present inventors have found that, when the secretion from adipose stem cells (hereinafter referred to as "ASC-CM") is administered to the skin at a specific dose, it promotes skin regeneration, promotes skin modification, can heal skin wounds or promotes skin rejuvenation. The inventors have also found that, when ASC-CM is administered at a specific dose to the scalp, it promotes the regeneration of the scalp, promotes the modification of the scalp, or promotes the rejuvenation of the scalp. Furthermore, the present inventors have found that, when ASC-CM is administered at a specific dose to the scalp, it promotes hair modification (modification of cuticles, amelioration of gray hair, increase in hair growth rate, increase in hair thickness, etc.).

According to the present invention, the following invention is provided.

(1) A pharmaceutical composition for topical administration, for use in modifying scalp or skin, comprising a secretion from adipose stem cells as an active ingredient, wherein 0.3 to 0.6 μg of the secretion is administered in terms of protein abundance per site in scalp or skin.

(2) A pharmaceutical composition for topical administration, for use in treating a wound, comprising a secretion from adipose stem cells as an active ingredient, wherein 0.3 to 0.6 μg of the secretion is administered in terms of protein abundance per site in wound.

(3) A pharmaceutical composition for topical administration for use in modifying hair, comprising a secretion from adipose stem cells as an active ingredient, wherein 0.3 to 0.6 μg of the secretion is administered in terms of protein abundance per site in scalp or skin.

(4) The pharmaceutical composition according to (3), wherein the hair modification is reduction of gray hair.

(5) The pharmaceutical composition according to (3), wherein the hair modification is amelioration of roughness of hair cuticles.

(6) The pharmaceutical composition according to (3), wherein the hair modification is amelioration of hair thickness or growth rate.

(7) The pharmaceutical composition according to any one of (1) to (6), which is administered at a rate of 1 site per 1 $cm^2$ to 4 $cm^2$ of a surface of scalp or skin.

(8) The pharmaceutical composition according to any one of (1) to (7), which is administered in a solution volume of 10 to 30 μL per site.

(9) The pharmaceutical composition according to any one of (1) to (8), wherein the administration interval is from twice a month to once every 6 months.

According to the present invention, it is advantageous in that it provides a pharmaceutical composition or a treatment method that may exert effects continuously even after the end of treatment.

BRIEF DESCRIPTION OF DRAWINGS

FIG. 2 is a diagram showing that gray hair changes to black at the root part by administration of ASC-CM.

FIG. 3 is a diagram showing the relationship between the administration of ASC-CM and the thickness of the fat layer of the skin. #1 to #5 indicate 1 to 5 months, respectively, after the treatment.

FIG. 4A is a schematic view of a head divided into nine.

FIG. 4B shows average values of ratings of the hair increasing effect on each of the 9 divided scalps in the ASC-CM 0.1 μg administration group (after first treatment; 6 to 9 months after the start of treatment; 2 years and 1 month to 3 years after the start of treatment, which is after the end of the treatment).

FIG. 4C shows the average values of the ratings of the hair increasing effect on each of the 9 divided scalps in the ASC-CH 0.4 μg administration group (after first treatment; 6 to 9 months after the start of treatment; 2 years and 1 month to 3 years after the start of treatment, which is after the end of the treatment).

FIG. 8A is the result of patient C.

In FIG. 8B, the data of patient A, the data of patient B and the data of patient C are shown in this order from the left.

DETAILED DESCRIPTION OF INVENTION

Figure 1:
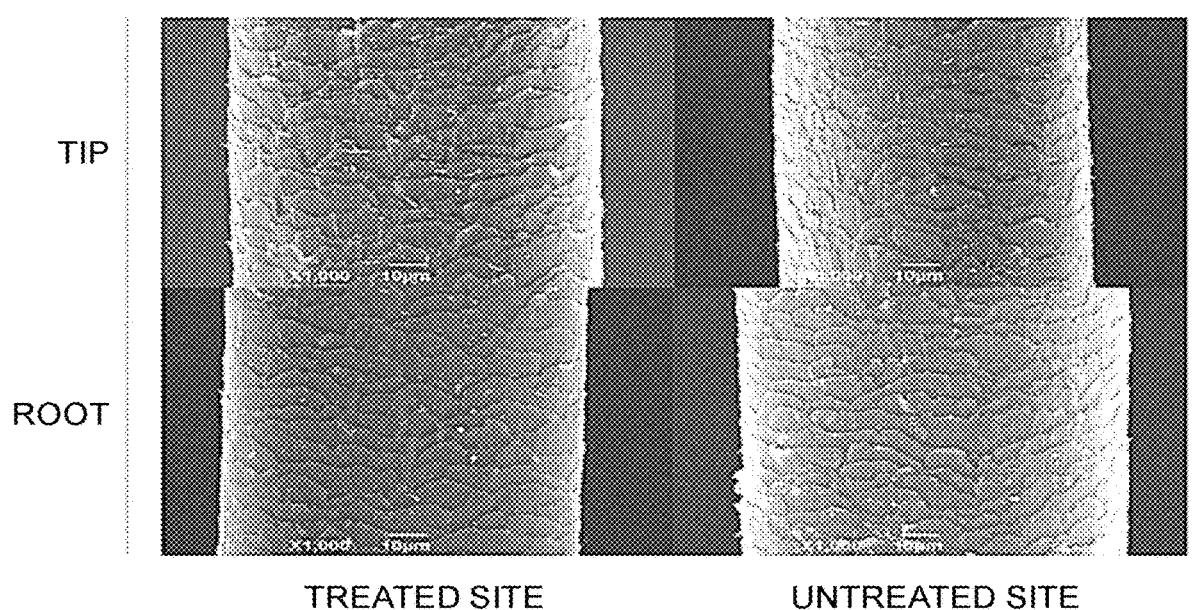
FIG. 1 is a photograph showing the effect of administration of ASC-CM on hair cuticles.

In the present description, "subject" means a mammal. Examples of mammals include a human (male and female).

In the present description, "adipose stem cell" means a cell present in adipose tissue, having stem cell properties and capable of differentiating Into both bone and fat. The adipose stem cells can be, for example, positive for one or more, for example all, selected from CD13, CD29, CD44, CD73, CD90, CD105 and CD166. The adipose stem cells can be, for example, negative for one or more, for example all, selected from CD14, CD31 and CD45.

In the present description, "secretion from adipose stem cells" means a substance secreted from adipose stem cells into a culture solution when the adipose stem cells are cultured in a solution. In the present description, the secretion from adipose stem cells are sometimes referred to as ASC-CM. Secretions from cells are thought to include various mediators between cells, and can include, for example, extracellular vesicles such as exosomes, proteins such as mRNA and cytokines, and the like.

In the present description, the "in terms of protein abundance" means that it is determined based on the mass of the contained protein.

In the present description, "scalp" refers to the region of the skin of the head, including the top of the head, and excluding the face, chin, and neck (including the ears). In the present description, "skin" is used in the sense that it includes the skin of the scalp and the skin other than the scalp.

In the present description, "modification" means improving, ameliorating, increasing or enhancing its quality. In the present description, "amelioration" is used in the sense that it includes becoming better than the current condition and making the poor part better.

In the present description, "hair" means hair that grows on the skin. In the present description, "scalp hair" means hair that grows on the scalp.

In the present description, "gray hair" means hair that is lacking pigments such as eumelanin (or true melanin) and/or pheomelanin, from the hair, in particular scalp hair, and that presents a gray color. In the present description, "black hair" means hair that contains eumelanin and presents a black color.

In the present description, a "cuticle" is a structure that covers the surface of hair, and is a structure that exists in the outermost layer of hair. The cuticle plays a role of protecting the hair from external stimuli and a role of preventing the loss of water or components from the inner cortex to the outside. The cuticles cover the hair from the root to the tip of the hair in a scaly manner.

In the present description, "wound" means physical damage to tissue. The wounds include wounds on the body surface.

In one aspect of the present invention,
(i) a pharmaceutical composition for topical administration, for use in modifying tissue (for example, scalp or skin), comprising a secretion from adipose stem cells as an active ingredient;
(ii) a pharmaceutical composition for topical administration, for use in treating a wound, comprising a secretion from adipose stem cells as an active ingredient; and
(iii) a pharmaceutical composition for topical administration, for use in modifying hair, comprising a secretion from adipose stem cells as an active ingredient are provided. In one aspect of the present invention, in the pharmaceutical composition according to the above (i) to (iii), 0.3 to 0.6 μg of the secretion can be administered in terms of protein abundance per site in scalp or skin.

In one aspect of the present invention,
(A) a pharmaceutical composition for topical administration, for use in modifying tissue (for example, scalp or skin), comprising a secretion from adipose stem cells as an active ingredient, wherein 0.3 to 0.6 μg of the secretion is administered in terms of protein abundance per site in scalp or skin;
(B) a pharmaceutical composition for topical administration, for use in treating a wound, comprising a secretion from adipose stem cells as an active ingredient wherein 0.3 to 0.6 μg of the secretion is administered in terms of protein abundance per site in wound; and
(C) a pharmaceutical composition for topical administration for use in modifying hair, comprising a secretion from adipose stem cells as an active ingredient wherein 0.3 to 0.6 μg of the secretion is administered in terms of protein abundance per site in scalp or skin are provided.

In one aspect of the present invention, the amount of secretion administered per site in scalp or skin can be, in terms of protein abundance, 0.3 to 0.6 μg, 0.35 to 0.5 μg, 0.35 to 0.45 μg, or about 0.4 μg. In one aspect of the present invention, an additional protein component such as a growth factor may be added to the above ASC-CM, but even in such a case, the dosage of ASC-CM can be, in terms of protein, 0.3 to 0.6 μg, 0.35 to 0.5 μg, 0.35 to 0.45 μg, or about 0.4 μg.

In one aspect of the present invention, the secretion from adipose stem cells is obtained in the culture supernatant by culturing adipose stem cells in a culture medium. In one aspect of the present invention, the secretion from adipose stem cells is obtained in the culture supernatant by culturing adipocytes in a serum free culture medium. In one aspect of the present invention, the secretion from adipose stem cells is obtained in the culture supernatant by culturing adipose stem cells in a culture medium (for example, serum-free culture medium) under hypoxic conditions. The culture medium for adipose stem cells can be a culture medium suitable for culturing adipose stem cells, for example, a culture medium such as DMEM, F12 and DMEM/F12, or for example, a chemically defined culture medium. Examples of hypoxic conditions include atmospheric conditions in which the oxygen concentration is 15% or less, 10% or less, or 5% or less (for example, 1.5% to 4%, for example, about 2% or 3%).

In one aspect of the present invention, the secretion from adipose stem cells can be obtained by culturing adipose stem cells in a DMEM/F12 culture medium in a hypoxic environment (for example, under a 2% $O_2$, 5% $CO_2$, 93% atmosphere) at 37° C. for 72 hours.

Adipose stem cells can be easily obtained from adipose tissue by those skilled in the art. Adipose stem cells can be obtained, for example, from abdominal adipose tissue. Abdominal adipose tissue can be obtained by abdominal liposuction. Purification of the adipose stem cells from adipose tissue can be performed, for example, as follows. The adipose tissue is washed, the cell mass is dissociated into single cells with type I collagenase, and filtered through a filter to remove tissue fragments and the like other than cells. It is washed as needed (for example, washed by suspending in normal saline solution or culture medium and centrifugation). Then, the adipose stem cells are separated according to cell density (specific gravity). For example, the adipose stem cells can be separated as floating cells by centrifuging with a Ficoll solution having a specific gravity of 1.077 g/cm (for example, Histopaque-1077). The obtained adipose stem cells can be confirmed by the expression of markers for adipose stem cells. Examples of markers for adipose stem cells include one or more, for example all, selected from CD13, CD29, CD44, CD73, CD90, CD105 and CD166. In addition, adipose stem cells can be confirmed by the fact that a specific marker is not expressed. Examples of such marker include one or more, for example all, selected from CD14, CD31 and CD45. In addition, the obtained adipose stem cells can be confirmed as having both the ability to differentiate into bone and the ability to differentiate into fat as an indicator.

The dose of the secretion from adipose stem cells can be determined by the protein content. The protein content can be determined by those skilled in the art according to conventional methods (for example, methods such as the Pyrogallol Red method and the Bradford method).

After administration, the secretion from adipose stem cells or the pharmaceutical composition containing the same ameliorates the scalp from the vicinity of the administration part, and its effect gradually propagates to the surroundings over time. Therefore, the effect of the invention can be propagated to the surroundings over time by being dotted on the scalp or the skin, or can be concentrated to shorten the time required for propagation. In one aspect of the present invention, the secretion is not particularly limited, and can be, for example, one site per 1 cm$^2$ to 10 cm$^2$, 1 cm$^2$ to 5 cm$^2$, 1 cm$^2$ to 4 cm$^2$, 1 cm$^2$ to 3 cm$^2$, 1 cm$^2$ to 2 cm$^2$, 0.5 cm$^2$ to 2 cm$^2$, 0.7 cm$^2$ to 1.5 cm$^2$. In one aspect of the present invention, the secretion can be administered at a dose density of, for example, one site or less per 0.5 cm$^2$, one site or less per 0.6 cm$^2$, one site or less per 0.7 cm$^2$, one site or less per 0.8 cm$^2$, one site or less per 0.9 cm$^2$, or one site or less per 1 cm$^2$. In one aspect of the present invention, the secretion from adipose stem cells or the pharmaceutical composition containing the same can be topically administered, for example, directly under the skin or from the dermis layer to the upper fat layer. Administration can be performed, for example, by injection.

In addition, for example, 10 µL to 50 µL, 15 µL to 30 µL, 15 µL to 25 µL, or about 20 µL of solution (note, however, that the solution contains the amount of active ingredient specified above) can be administered per site.

The administration site can be selected as appropriate, but it can be administered, for example, to the entire scalp, or to a part of the scalp that is poorer compared to the rest of the entire scalp.

Moreover, surprisingly, the present inventors have found that the effect easily propagates to the surroundings when administered to a relatively good site of the entire scalp. The good part is highly responsive to the pharmaceutical composition of the present invention, and the effect propagates and extends to the area around the administration site. The ameliorating effect by propagation appears strongly nearer to the administration site, but extends over several centimeters (for example, 1 cm to 4 cm) from the administration site. Therefore, it can be administered to a relatively good site of the scalp. In addition, since the ameliorating effect propagates from the good site to the relatively poor site, the treatment effect to the poor site can be obtained even when only administering to the relatively good site.

Therefore, it may be administered to a relatively good site of the scalp, and the effect of propagation may be used to try to ameliorate the poor part. In addition, when an amelioration is obtained at a relatively poor site, the responsiveness to the pharmaceutical composition of the present invention is increased. Therefore, when it is administered to a relatively good site of the scalp and the amelioration of the poor part has progressed by the effect of propagation, then the pharmaceutical composition of the present invention may be administered to the part that was poor.

Each time ASC-CM is administered, tissue stimulation, macrophage activity and juvenile adipose cell activity at the administration site are thought to rise, and repair function to increase. It is desirable to administer after examining the patient s symptoms (condition) and the degree of amelioration.

In one aspect, 15 µg/mL to 25 µg/mL (for example, about 20 µg/mL) of ASC-CM in terms of protein abundance can be topically administered to the scalp in an amount of 15 µL to 25 µL (for example, about 20 µL) per site. In one aspect, the topical administration can be 150 sites to 250 sites (for example, about 200 sites) or 250 sites to 800 sites per scalp of an adult, and the number of administration sites can be determined as needed. Here, the term "about" means that it includes the numerical range of ±10% or ±5% of the numerical value following this term.

The secretion from adipose stem cells or the pharmaceutical composition containing the same is not particularly limited, and can be administered, for example, at an administration interval of twice a month to once every 6 months, twice a month to once every 5 months, twice a month to once every 4 months, twice a month to once every 3 months, twice a month to once every 2 months, 1.5 times a month to once every 1.5 month, or 1.2 times a month to once every 1.2 months, for example, about once a month.

The secretion from adipose stem cells or the pharmaceutical composition containing the same has a modifying effect on the scalp and skin even with a single administration, and this effect can be sustained. Therefore, administration may be performed once or plural times. The secretion from adipose stem cells or the pharmaceutical composition containing the same can also be administered continually until the treatment is completed or until the patient is satisfied. In particular, according to the present invention, the modifying effect on the scalp and skin appears from the part in good condition and appears later on the part in poor condition. Therefore, the treatment period can vary depending on the condition of the scalp and skin. The treatment period with the secretion from adipose stem cells or the pharmaceutical composition containing the same can be, for example, a minimum of one treatment to 3 years, a minimum of one treatment to 2 years, a minimum of one treatment to 1.5 years, a minimum of one treatment to 1 year, a minimum of one treatment to 8 months, a minimum of one treatment to 6 months, or a minimum of one treatment to 4 months.

In one aspect of the present invention, the pharmaceutical composition according to (A) can be a pharmaceutical composition for use in the rejuvenation or promoting the rejuvenation of the scalp or skin. In one aspect of the present invention, the pharmaceutical composition according to (A) can be a pharmaceutical composition for use in the regeneration or promoting the regeneration of the scalp or skin. In one aspect of the present invention, the pharmaceutical composition according to (A) can be a pharmaceutical composition for use in the activation of the scalp or skin. In one aspect of the present invention, the pharmaceutical composition according to (A) can be used in combination with a hair increasing agent or a hair growth agent.

In one aspect of the present invention, the pharmaceutical composition according to (B) can be used to treat a wound. In the present invention, the treatment of a wound can be wound healing, promoting wound healing, or accelerating wound healing.

By ameliorating the scalp, the effect also extends to the hair itself. And, as shown in Examples described later, the hair ameliorating effects include a reduction of gray hair, a reduction of the weight of the gray hair part, and a reduction of the proportion of gray hair, an amelioration of cuticle roughness, and an amelioration of hair thickness and growth rate. Therefore, in one aspect of the present invention, the pharmaceutical composition according to (C) can be a pharmaceutical composition for use in reducing gray hair. The reduction of gray hair includes a reduction in the number of gray hairs, a reduction in the weight of the gray hair parts, and a reduction in the proportion of gray hair. The reduction of gray hair can be accompanied by an increase in the number of hairs pigmented with various melanins, an increase in the weight of such hair part, and an increase in the proportion of such hair. In one aspect of the present invention, the pharmaceutical composition according to (C) can be a pharmaceutical composition for use in ameliorating the roughness of hair cuticles. Ameliorating the roughness of the hair cuticles includes increasing the degree of cuticle alignment and reducing the region of disordered cuticles. In one aspect of the present invention, the pharmaceutical composition according to (C) can be a pharmaceutical composition for use in ameliorating the hair thickness or growth rate. Amelioration of the hair thickness includes thickening the hair, increasing the number of thick hairs, and increasing the proportion of thick hair. Amelioration of the growth rate include increasing the number or proportion of hair having a growth rate of, for example, 10 mm or more, 11 mm or more, 12 mm or more, 13 mm or more, 14 mm or more, 15 mm or more, 16 mm or more, 17 mm or more, 18 mm or more, 19 mm or more, 20 mm or more, or 21 mm or more per month.

In one aspect of the present invention, (a) a method for modifying scalp or skin in a subject in need thereof (or in a site in need thereof), comprising topically administering 0.3 µg to 0.6 µg of secretion from adipose stem cells in terms of protein abundance per site in scalp or skin;

(b) a method for treating a wound in a subject in need thereof, comprising topically administering 0.3 µg to 0.6 µg of secretion from adipose stem cells in terms of protein abundance per site in wound; and (c) a method for modifying hair in a subject in need thereof, comprising topically administering 0.3 µg to 0.6 µg of secretion from adipose stem cells in terms of protein abundance per site in scalp or skin are provided.

In one aspect of the present invention, ($\alpha$) a use of the secretion from adipose stem cells in the manufacture of a pharmaceutical preparation for topical administration, for use in modifying scalp or skin (wherein 0.3 µg to 0.6 µg of the secretion is administered in terms of protein abundance per site in scalp or skin);

($\beta$) a use of the secretion from adipose stem cells in the manufacture of a pharmaceutical preparation for topical administration, for use in treating a wound (wherein 0.3 µg to 0.6 µg of the secretion is administered in terms of protein abundance per site in wound); and ($\gamma$) a use of the secretion from adipose stem cells in the manufacture of a pharmaceutical preparation for topical administration, for use in modifying hair (wherein 0.3 µg to 0.6 µg of the secretion is administered in terms of the protein abundance per site in scalp or skin) are provided.

In one aspect of the present invention, the pharmaceutical composition can comprise an excipient (for example, a solvent, a cosolvent, a solubilizer, a wetting agent, a suspending agent, a thickener, an emulsifier, a chelating agent, a buffer solution, a pH adjuster, an antioxidant, a reducing agent, an antibacterial agent, a preservative, a filler, a protective agent, or an isotonic agent), in addition to the secretion from adipose stem cells. In one aspect of the present invention, the pharmaceutical composition can be in the form of an injection. In one aspect of the present invention, the pharmaceutical composition may be administered topically, for example, intradermally or subcutaneously.

EXAMPLES

Example 1: Hair Increasing Effect by Adipose Stem Cell Secretion (1) Preparation of Adipose Stem Cell Secretion (Hereinafter also Referred to as "ASC-CM")

The secretion of adipose stem cells was prepared as follows.

Adipose tissue was collected by abdominal liposuction from healthy adult female donors (5 people, ages 20 to 21 years) who had had a virus check (HIV, HBV, HCV) by blood test, and the adipose-derived stem cells (ADSCs) were separated by the following method. After centrifugation at 300 g×10 minutes, 0.075% type I collagenase (Sigma-Aldrich, USA) was added and treated at 37° C. for 45 minutes. Phosphate buffer solution (PBS) was added and the solution was filtered through a 70 µm filter. Then, after addition of a small amount of α-modified Eagle medium (Invitrogen, USA) and centrifugation at 300 g×10 minutes, PBS was added and the solution was filtered through a 70 µm filter. After performing centrifugation at 840 g×10 minutes using histopaque-1077 (Sigma-Aldrich, USA), the supernatant was discarded and the cells floating on histopaque-1077 were collected to obtain ADSCs.

According to the guidelines of the FDA (US Food and Drug Administration) and KFDA (Korean Food and Drug Administration), virus tests of the adipose tissue and washed cells and bacterial culture tests were performed to eliminate infection with unwanted bacteria. A Dulbecco test was performed to eliminate the infection of unwanted bacteria. Culture was performed using a medium containing Dulbecco's Modified Eagle's Medium (DMEM), 10% Fetal Bovine Serum (FBS) of a New Zealand Species and 100 units/ml penicillin and 100 units/ml streptomycin, in a 5% carbon dioxide environment at 37° C. for 3 to 5 days. This process was repeated four more times to obtain $4 \times 10^5$ ADSCs (adipose-derived stem cells) per 100 $mm^2$. ADSCs were washed with PBS and fresh DMEM/F12 serum-free culture medium (Invitrogen-Gibco-BRL, USA) was added. ADSCs were maintained in a hypoxic environment (2% $O_2$, 5% $CO_2$, 93% $N_2$) for 72 hours to promote the secretion of ADSCs. Then, by centrifugation at 300 g×5 minutes followed by filtering using a 0.22 µm syringe filter, a culture supernatant of the adipose-derived stem cells was obtained. At this point, virus tests and bacterial culture tests were performed again to eliminate bacterial and viral infections. Finally, the secreted component was purified using 3-kDa molecular-weight cut-off Centricon tubes (Millipore Corp, USA) to obtain ASC-CM. The protein content of ASC-CM was confirmed by the Bradford method and the Pyrogallol Red method.

(2) Administration of ASC-CK to Patients with Thin Hair 0.1 µg (n=14), 0.2 µg (n=3), 0.4 µg (n=9), 0.6 µg (n=9), or 0.8 µg (n=4) of ASC-CM per site in terms of protein abundance was subcutaneously administered using a syringe to the scalp (right half, left half or both) of patients with thin hair (21 males and 16 females aged 25 to 72 years). ASC-CM was administered to two patients at different doses on the right and left half of the scalp. In this case, 20 μL per site was administered to 200 sites of the scalp at the concentration to be the above dose. Each concentration was administered to 100 sites when treating half of the scalp. In this case, it was administered to the scalp at a dose density of 1 cm$^2$ to 4 cm$^2$. Administration was performed at a frequency of once a month except in exceptional cases, and the administration period was 6 to 10 months (8 months on average). Observations were made one month after the end of administration in all cases. The group administered with X μg in terms of protein abundance per site of skin surface is referred to as "X μg administration group", "X μg/site administration", or the like throughout Examples. Hereinafter, when the dosage of ASC-CM is described as 0.4 μg, it means that 0.4 μg in terms of protein abundance was administered without exception.

The change over time in the number of hairs after treatment with respect to the number of hairs at the first administration was visually observed. Consent to photographing with a trichogram before treatment and at each treatment stage was obtained. Both corners of the patient's eyes were extended to the head side and two points crossing the line connecting both ears and top of the head were tattooed with India ink, and a 2-cm area centered on the marking was shaved monthly at a timing of 3 days before administration. The trichograms were taken every time centered on the marking (Canon Power Shot A520, Tokyo, Japan). At this time, the photograph was taken with the glass plate pressed against the scalp and the hair laid down, so that the hair length could be visible. It was carried out by visually measuring the hair within a circle of 11 mm in diameter (95 mm$^2$ area) centered on the tattoo contained in the photographing range.

The results are as shown in Table 1.

TABLE 1

Dose dependency of ASC-CM administration

| Dose | After 6 months | After 8 months | After 10 months |
| --- | --- | --- | --- |
| 0.1 μg administration group | +4% | +5% | ND |
| 0.2 μg administration group | −3% | −15% | −13% |
| 0.4 μg administration group | +1% | −6% | −8% |
| 0.6 μg administration group | +1% | −10% | −16% |
| 0.8 μg administration group | +3% | −2% | −7% |

ND: no effective number of data was obtained

As shown in Table 1, in the group administered with 0.1 μg (20 μL of 5 μg/ml) in terms of protein abundance per site (0.1 μg administration group), although the effect of increasing the number of hairs was confirmed for the time of the first administration, in contrast, no noticeable effect of increasing the number of hairs was observed in the 0.2 μg administration group, 0.4 μg administration group, 0.6 μg administration group and 0.8 μg administration group, but rather, a reduction in the number of hairs was observed after 8 months or 10 months. However, with the administration of only the ASC-CM component, the results were not stable as described above, and it was considered to be difficult to draw a definitive conclusion on the evaluation based on the number of hairs.

Thus, in the treatment of thin hair, no dose dependency was observed, and it became clear that the administration of a high dose of 0.2 μg or more in terms of protein abundance per site instead did not increase the number of hairs. From these results, it was considered that it is necessary to administer 0.1 μg in terms of protein abundance per site for the treatment of patients with thin hair.

These results are data consistent with the results already reported by the inventors (all performed at 0.1 μg/site) (Fukuoka et al., The American Journal of Cosmetic Surgery, 29 (4); 273-282, 2012).

Example 2: Change in the Hair Quality

In the present Example, it was examined whether an amelioration was observed for the hair cuticles before and after treatment.

The hair of the ASC-CM 0.4 μg administration group (administered once a month) is collected and the hair of the test site (the site corresponding to 2 months before treatment and the site 3.5 months after the start of the treatment, considering the growth rate of the patient's hair) is adhesively fixed to a fixing plate with a resin on the day of collection or on the next day. The fair was subjected to carbon fixation on the next day or the day after next, and the state of the hair cuticles was observed by a scanning electron microscope according to the conventional method on the same day. The hair of the non-treated part of the same patient was used as a negative control. Then, the newly grown part of the hair (root side), and the existing part (tip side) were compared. A representative example is shown in FIG. 1.

As a result, for the treated hair, it was observed that while the cuticles were rough on the tip side, the cuticles were smooth on the root side, which is the newly grown part, and the difference in hair quality was clearly ameliorated. On the other hand, in the hair of the non-treated part of the negative control, cuticle roughness was observed on both the root and the tip side, and the quality ameliorating effect was not observed in the non-treated part.

Similar evaluations were performed on more patients (3 patients) (ASC-CM 0.4 μg, administered once a month, administered for 3 to 5 months). The evaluations were carried out one month after the last administration based on the electron microscopic image based on the following ratings. The evaluations were carried out by seven doctors or the like who were healthcare professionals. The average values of the ratings were calculated.

Hair Quality Evaluation Rating Sheet 5 points: The cuticles are smooth and no roughness is visible.

4 points: The cuticles are smoother than average, bur some roughness is observed.

3 points: The cuticles' smoothness is average.

2 points: The cuticles are rougher than average and some peeling is observed.

1 point: The cuticles are overall rough and peeling is observed overall.

The results are as shown in Table 2.

TABLE 2

Change hair quality between Treated site and Untreated site

| | Treated site | Untreated site |
| --- | --- | --- |
| Patient 1 | 3.71 | 3 |
| Patient 2 | 3 | 2.14 |

For patient 3, the treatment had already started before the present Example. However, observation according to the present Example was started, and similar changes in hair quality were confirmed after 4 months.

As described above, in the 0.4 µg administration group, changes in hair quality were observed after administration. On the other hand, no ameliorating effect on hair quality was observed in the 0.1 µg administration group as in the negative control.

For patient 3, the treatment was started before the present Example, but an amelioration of the hair quality by the ASC-CM 0.4 µg administration was clearly observed.

Example 3: Change in Hair Quality

In this example, the ameliorating effect was examined before and after treatment, focusing on the color of hair (gray hair).

The area of gray hair after 6 months to 16 months from the start of the treatment (average 9.4 months; average 9.2 times of treatment) was examined in the ASC-CM 0.4 µg administration group (n=5, 54 to 61-year-old males) and was compared with that before treatment. As a result, as shown in Table 3, an average reduction of about 38% in area ratio was observed.

TABLE 3

Reducing effect on gray hair area by ASC-CM administration

| ID | Age | First time (cm2) | M (cm2) | Increase/ Reduction (%) | Elapsed time |
|---|---|---|---|---|---|
| 1 | 60s male | 280.1 | 156.8 | −46% | 12 months |
| 2 | 60s male | 240.1 | 205.8 | −14% | 1 year 4 months |
| 3 | 60s male | 142.1 | 102.9 | −28% | 6 months |
| 4 | 60s male | 142.1 | 53.9 | −62% | 6 months |
| 5 | 60s male | 127.4 | 68.6 | −46% | 7 months |
|   |          | 188.16 | 117.6 | −38% |   |

In FIG. 2, the ASC-CM 0.4 µg administration group (67-year-old female, 5 treatments, 6 months from the start of treatment, and 61-year-old male, 8 treatments, 4 months follow-up, 12 months from the start of treatment) shows that the root part of the gray hair turned black after treatment. As shown in FIG. 2, it is shown that the part which was already gray hair is still gray, but the part which has newly grown after the treatment is black.

Example 4: Verification of the Modifying Effect on Scalp

Although the modification of hair was shown above, the modification of the scalp on which the modification of hair is based on was verified.

Changes in the thickness of the fat layer in the subcutaneous tissue of the scalp were observed by echography using a 10 Mz probe. In this test, the region from the sebaceous gland region to the lower part is measured, and it is considered that the thickness of roughly the region to the dermis layer is measured (however, the dermis layer is not included in the measurement value). The results are as shown in FIG. 3. In FIG. 3, the measurement values of a patient administered 0.4 µg of ASC-CM/site once a month are shown. "#n" in FIG. 3 indicates n months after the treatment.

As a result, as shown in FIG. 3, no significant change was observed in the thickness of the fat layer 5 months after the start of the treatment.

In addition, it became clear that no scalp modification occurred in the ASC-CM 0.1 µg administration group, while scalp modification occurred in the ASC-CM 0.4 µg administration group, with the ASC-CM 0.1 µg administration in previous studies, an effect of increasing the number of hairs over a short period was observed, but no modifying effect on the scalp was observed. On the other hand, with an ASC-CM administration at a higher dose (0.4 µg/site), although the effect of increasing the number of hairs over a short period was weak, it became clear that the modifying effect on the scalp is high. Although the effect of increasing the number of hairs over a short period was seemingly weak in the high-dose administration group, amelioration of the hair quality through modification of the scalp (change from gray hair to black hair or amelioration of the cuticle roughness) had occurred. In addition, it has been suggested that, in the long term, a hair increasing effect can also be expected through the modification of the scalp.

Example 5: Scalp Modifying Effect by Site

In the present Example, the effect of the treatment was observed by dividing the scalp into nine regions from the top. This was to achieve a more accurate evaluation by assessing separately the influence on the good parts (parts with many hairs) and the influence on the poor parts (parts with few hairs) when examining the treatment effect, since good parts and poor parts coexisted in each patient. In addition, a long observation period was set, since it was thought from the previous Examples that although scalp modification occurs at a high dose administration, a long observation period is necessary because modification takes time.

In particular, it was examined whether the modification of the scalp still produced a hair increasing effect also after the treatment ended. For this purpose, the treatment period was set to about 8 months, at which time the treatment was ended and only the hair increasing effect vas observed without treatment thereafter.

Nine regions were set according to the following criteria. Specifically, the head image taken from the top of the head was regarded as an ellipse, and divided into nine regions by dividing the major axis into three equal parts and the short axis into three equal parts. In FIG. 4A, a schematic drawing is shown to indicate how the nine sections of the head were divided.

For patients with thin hair (n=12), 0.1 µg (0.1 µg administration group; n=4) or 0.4 µg (0.4 µg administration group; n=8) of ASC-CM per site, was administered once a month for 6 months (n=1), 8 months (n=10) and 10 months (n=1) and then the treatment was ended. The observation and evaluation of the hair increasing effect was performed over the next three years. The hair increasing effect vas assessed by a total of 10 healthcare professionals including 7 doctors. The ratings were marked by each evaluator based on the following rating sheet and the average value was calculated.

Rating of Hair Increasing Effect 5 points: Almost normal
4 points: Less than 20% see-through
3 points: Less than 40% see-through
2 points: Less than 60% see-through
1 point: Less than 80% see-through The results are as shown in FIGS. 4B and 4C. FIGS. 4B and 4C show the average point of the ratings for each section divided into nine regions.

As shown in FIG. 4B, in the 0.1 µg administration group, a high hair increasing effect was observed overall early on, but when the treatment was stopped, the effect also disappeared immediately.

In contrast, in the 0.4 μg administration group, as shown in FIG. 4C, although the early hair increasing effect was limited, the hair increasing effect remained even after stopping treatment 8 months after the start of the treatment, and in the end, a very satisfactory hair increase was achieved.

This suggests that the treatment was not fundamental with the 0.1 μg administration group, while a substantial ameliorating effect of the scalp was achieved with the 0.4 μg administration group, and thus that it was closer to a fundamental treatment of hair increase.

Furthermore, in the 0.4 μg administration group, the hair increasing effect appeared first from the high score area (where the scalp condition was good), and in the low score area (where the scalp condition was poor), the hair increasing effect appeared later. This is thought to be due to the mechanism of the scalp, in which it requires time to ameliorate the scalp, but when the scalp is ameliorated, the hair increasing effect appears.

Example 6: Ameliorating Effect and Histology of the Scalp

In the present Example, it was examined what kind of change in histology is observed as the scalp ameliorates. In the present Example, the increase and decrease of collagen and the rejuvenation of adipocytes were observed.

(1) Change in Collagen Image

First, the increase and decrease of collagens other than type III and type III collagen were observed. Specifically, a section of the scalp tissue (surface from the epidermis to the skull) was prepared and type I collagen and type III collagen were stained using a Picrosirius Red Stain Kit reagent (Polysciences, Inc., Cat 4: 24901-250) according to the manufacturer's instruction manual. Type I collagen was stained in yellow and type III collagen was stained in green. In addition, collagens other than type III are stained in yellow to red. The observed image was stored as a digital image in gray scale, yellow to red and green were each selected and extracted as an image by Photoshop (trademark), and then the amount of collagen (collagens other than type III and type III collagen) was estimated from each pixel's intensity As a result, in human specimens (n=3), type III collagen was found in tissues before treatment, and it was observed that type III collagen tended to decrease as the treatment with ASC-CM 0.4 μg administration (once a month) progressed. In addition, it was observed that collagens other than type III tended to increase overall with treatment.

Figure 5A:
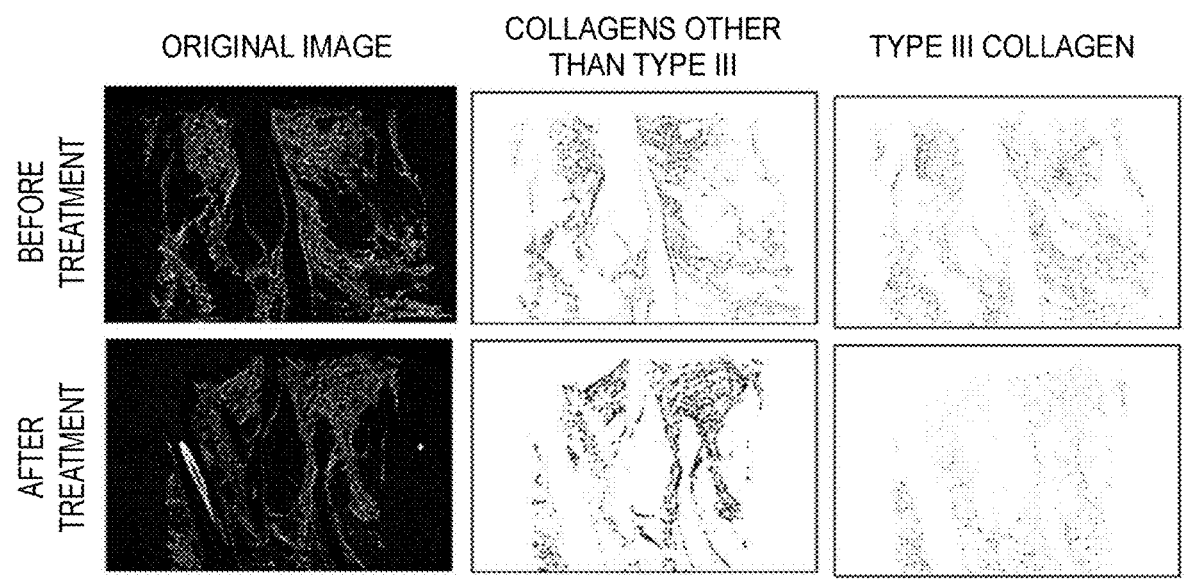
FIG. 5A shows the histological staining of collagen in skin tissue before and after treatment.
Figure 5B:
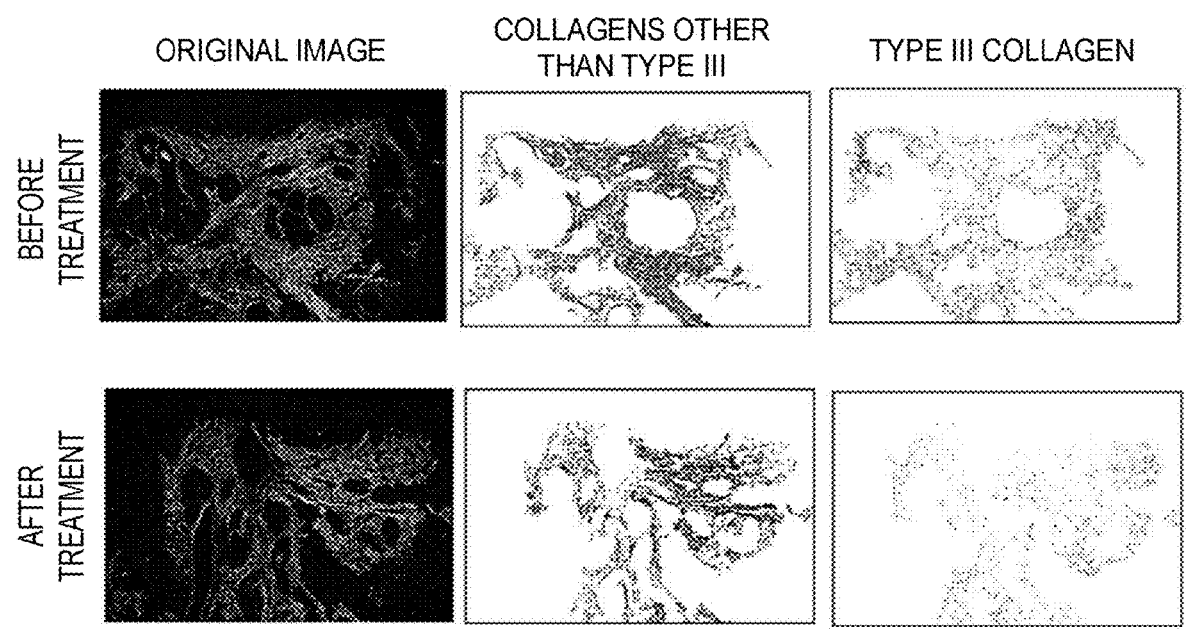
FIG. 5B shows the histological staining of collagen in skin tissue before and after treatment.

Representative examples of stained images (2 patients) are shown in FIGS. 5A and 5B. FIGS. 5A and 5B show grayscale images based on the intensity of yellow to red (collagens other than type III) images and green (amount of type III collagen) images, respectively, together with color photographs. FIG. 5A shows the patient's scalp tissue 4 months after the start of the treatment, and FIG. 5B shows the patient's scalp tissue 6 months after the start of the treatment. In both cases, collagens other than type III and type III collagen were both expressed on the untreated side, but on the treated side the amount of type III collagen had decreased (decreased to about 66%). It can be seen that the collagens other than type III have increased (increased to about 113%).

(2) Rejuvenation of Adipocytes

Next, the rejuvenation of adipocytes was observed. As the adipocytes grow, most of the cytoplasm becomes fat droplets to store fat in the cytoplasm and they become enlarged. Therefore, large cells represent mature old cells, and small cells are considered to be immature new cells. More specifically, tissue sections of the back skin of Wistar rats (n=3) to which ASC-CM was administered once were observed to confirm the changes in the size of the adipocytes m the fat layer. The images of the adipocytes were approximated to a circle and classified into S, M or L based on their diameter. Cells having a diameter of 25 μm or less were counted as "S", cells having a diameter of more than 25 μm and 36 μm or less as "M", and cells having a diameter of more than 36 μm as "L". The results are as shown in FIG. 5C.

Figure 5C:
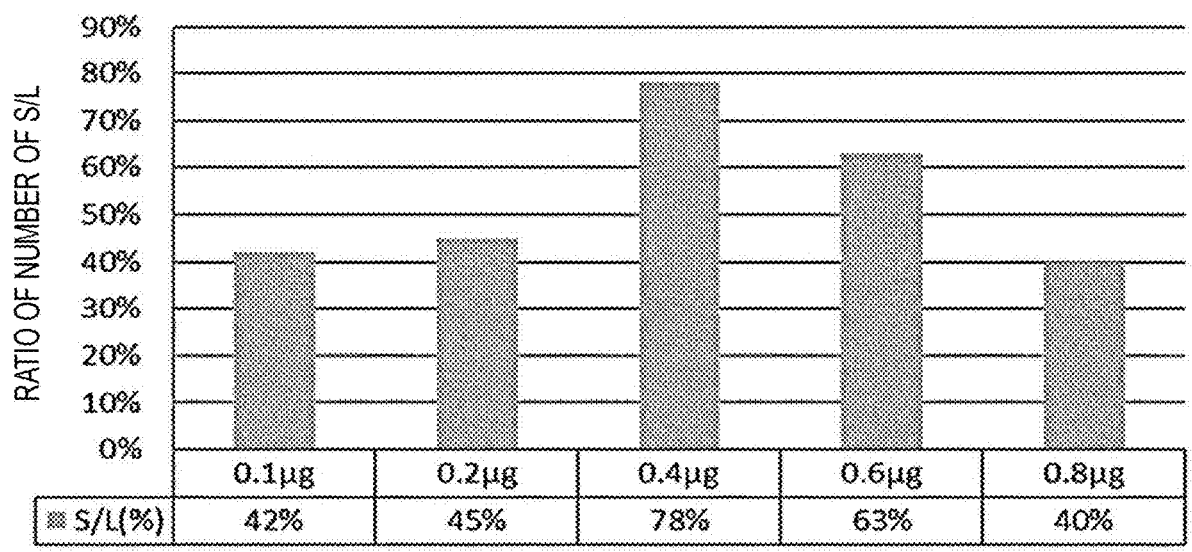
FIG. 5C is a diagram showing the dose dependency of ASC-CM administration on the size of an adipocyte.

As shown in FIG. 5C, in the ASC-CM 0.4 μg administration group, the ratio of "S" adipocytes to "L" adipocytes had significantly increased 4 weeks after the treatment. In the ASC 0.1 μg administration group, no change resulting from the administration was observed in the size of the adipocytes in the fat layer.

A decrease in type III collagen, an increase in collagens other than type III and an increase in small adipocytes are results suggesting that the tissue may be regenerated by ASC-CM.

Example 7: Effect on Wound Healing

The previous Examples suggested that the administration of a specific dose of ASC-CM may regenerate skin tissue. In the present Example, the tissue repair ability of ASC-CM was verified by topically administering ASC-CM to a wound site.

Preparation of the wounds: The backs of 12-week-old Wister rats (n=3) were shaved with a hair clipper, one circular skin full-thickness defect of 8 mm in diameter was made on each of the left and right sides of the head and tail sides, to create four skin full-thickness defects per body.

Administration method of ASC-CM: 0.02 ml containing 0.1 μg, 0.2 μg, 0.4 μg or 0.8 μg of ASC-CM in terms of protein abundance was injected subcutaneously at 4 sites 4 mm away from the wound margin (upper and lower, right and left of the wound).

Rating of Wound Healing 5 points: Healed 4 points: The reduction ratio of the wound site area is 70% or more 3 points: The reduction ratio of the wound site area is 50% or more and less than 70%

2 points: The reduction ratio of the wound site area is 20% or more and less than 50%

1 point: The reduction ratio of the wound site area is less than 20%

Figure 6:
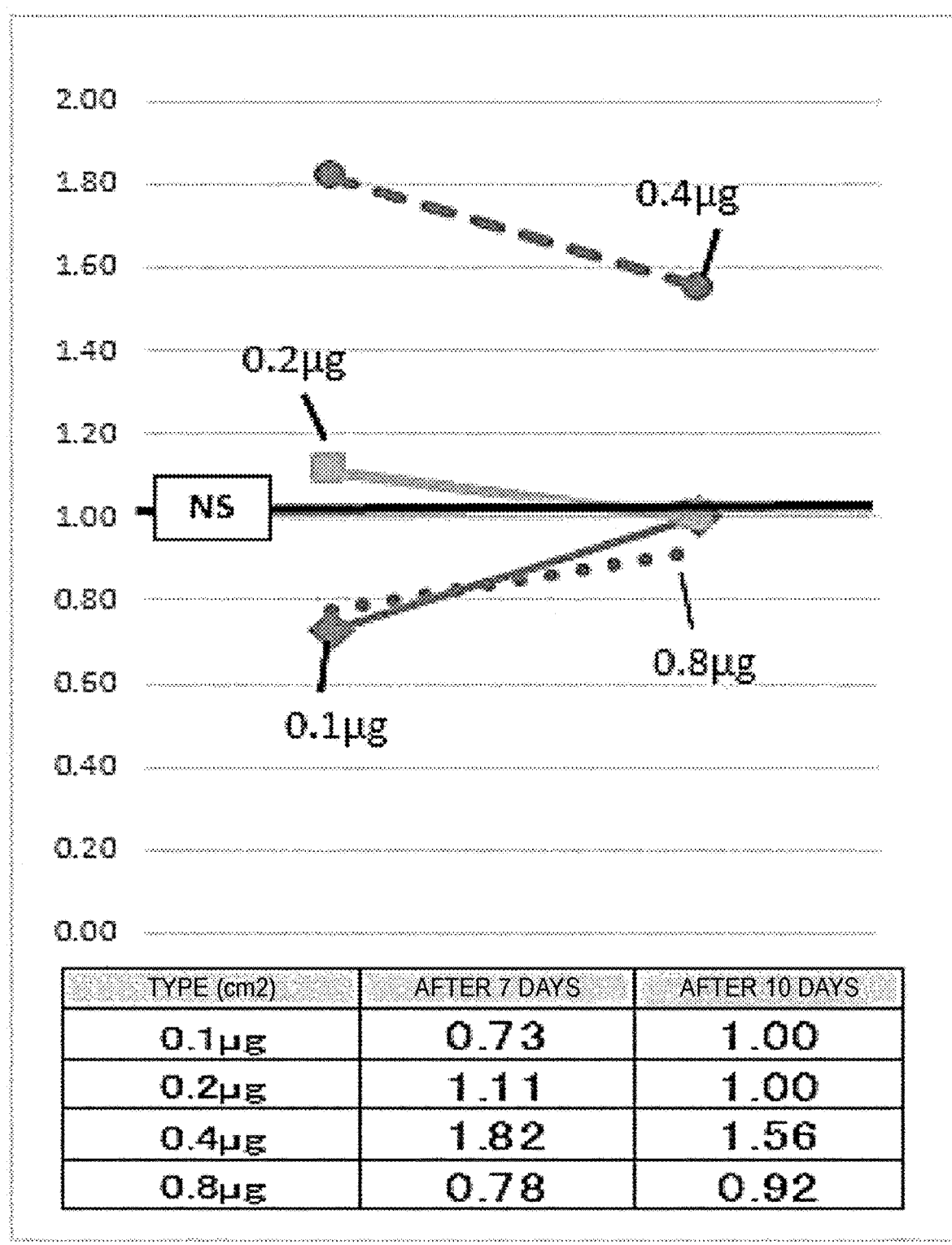
FIG. 6 shows the relationship between the ASC-CM administration dose and the healing effect on wounds.

The results were obtained by dividing the above ratings by the rating for normal saline solution. The results are as shown in FIG. 6. As shown in FIG. 6, the wound healing was significant in the ASC-CM 0.4 μg administration group. In addition, in the ASC-CM 0.1 μg administration group and 0.8 μg administration group, the wound healing effect was equivalent to that of normal saline solution.

It became clear that ASC-CM has a modifying effect on the skin at a high dose, and that the effect is particularly high in each 0.4 μg administration group. In addition, the modifying effect on the skin was beneficial not only for ameliorating hair increase and hair quality but also for ameliorating wound healing. It was a very interesting result that the concentration at which the modification of the scalp was considered to occur coincided with the concentration at which the wound healing effect was high.

Example 8: Detection of Tissue-Resident M2-Like Macrophages and PPARγ-Positive Adipocytes in Scalp Tissue After ASC-CM Administration It has been reported that when tissue regeneration occurs in peripheral tissues (especially skin and scalp), an increase in tissue-resident M2-like macrophages or an increase in PPARγ-positive adipocytes occurs (Festa E et al., Cell, 146: 761-71, 2011). Therefore, in the present Example, it was examined whether an increase in tissue-resident M2-like macrophages or an increase in PPARγ-positive adipocytes occurred in scalp tissue after ASC-CM administration. In addition, it was confirmed whether an increase in Ki67-positive cells occurred as an activation marker for cell proliferation in the scalp. Tissue-resident M2-like macrophages were detected as CD68-positive cells or CD163-positive cells.

Tissue sections of the scalp (3 mm diameter punch section from the surface of scalp to the top of the skull periosteum) of several adult ASC-CM 0.4 µg administration groups (administered once a month) were fixed according to the conventional method and immunohistological staining was performed. They were collected 4 months after treatment and 6 months after treatment to see the changes over time. Moreover, the primary antibodies and secondary antibodies used for staining in the present Example were as follows.

TABLE 4

Primary antibodies and secondary antibodies used for immunohistological staining

| | Name | Product number | Lot | Manufacturer information | |
|---|---|---|---|---|---|
| CD68 | | | | | |
| Primary | CD68 Mouse monoclonal antibody | NCL-CD68-KP1 | 211710 | NOVOCASTRA | United Kingdom |
| Secondary | EnVision + System-HRP Labelled Polymer Anti-Mouse | K4001 | — | DaKo | Denmark |
| CD163 | | | | | |
| Primary | Anti Human Macrophage Surface Antigen Monoclonal Anitbody | KT013 | TG201213 | Trans Genic Inc. | Japan |
| Secondary | EnVision + System-HRP Labelled Polymer Anti-Mouse | K4001 | — | DaKo | Denmark |
| PPARγ | | | | | |
| Primary | PPARγ (C26H12) Rabbit mAb | #2435 | No. 4 | Cell Signaling Technology | United States |
| Secondary | EnVision + System-HRP Labelled Polymer Anti-Rabbit | K4003 | — | DaKo | Denmark |

In addition, the results of the immunohistological staining showed that the number of CD68-positive cells was on average 18.5 (n=2) in the whole section of 3 mm punch without treatment, but was 24 (n=1) 4 months after the start of the treatment, and on average 76 (n=2) 6 months after treatment, thus an increase in CD68-positive cells was observed in all patients. Furthermore, the number of CD163-positive cells was on average 36 (n=2) in the whole section of 3 mm punch without treatment, but on average 69.5 (n=2) 6 months after treatment, thus an increase in CD163-positive cells was observed in all patients. In addition, the number of PPARγ-positive cells was on average 33.5 (n=2) in the whole section of 3 mm punch without treatment, but was on average 88.5 (n=2) 6 months after treatment, thus an increase in PPARγ-positive cells was observed in all patients.

Figure 7:
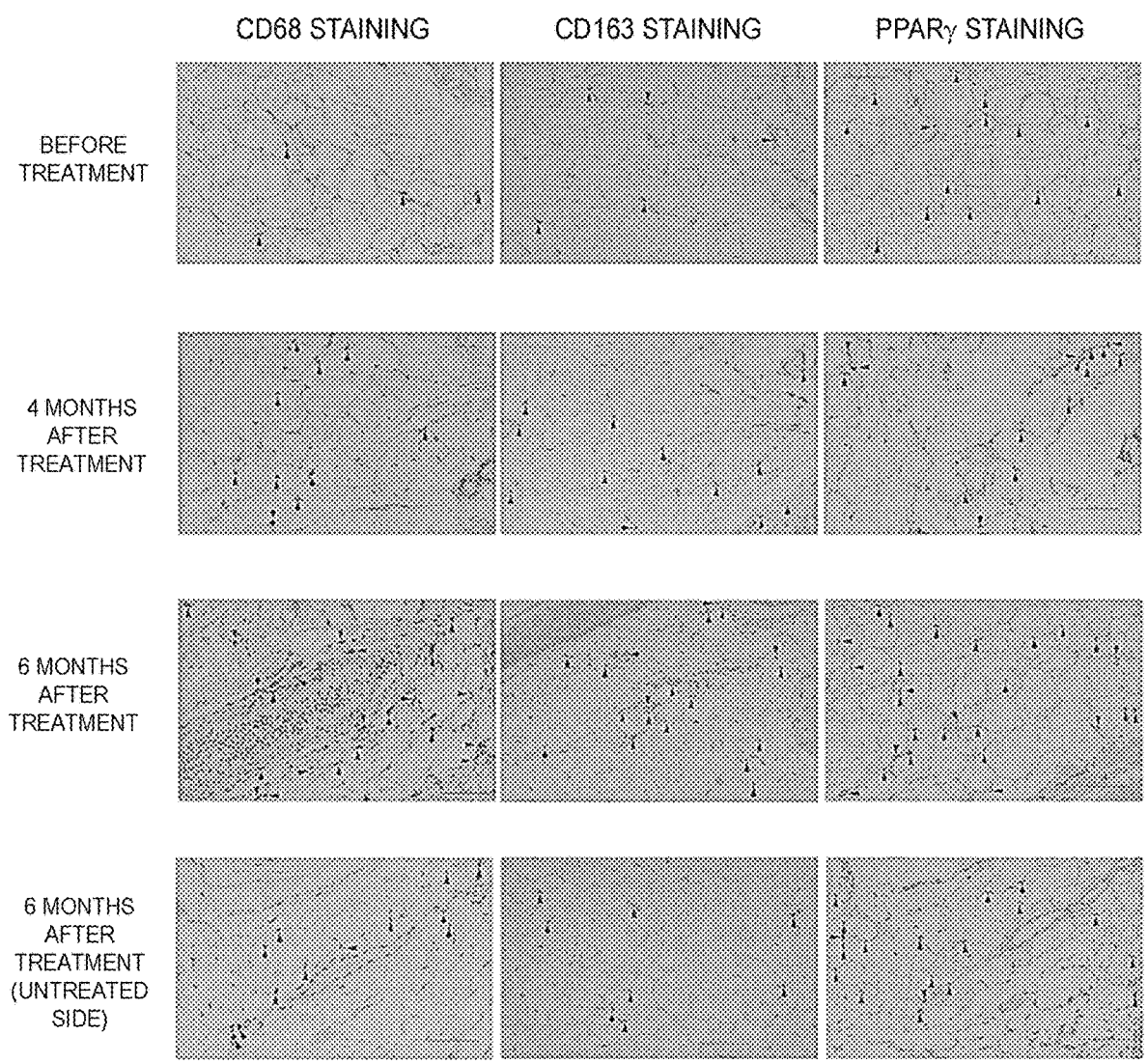
FIG. 7 shows the results of immunohistological staining (staining of CD68-positive macrophages, staining of CD163-positive macrophages and staining of PPARγ-positive adipocytes) of the scalp fat layer in the ASC-CM 0.4 μg administration group.

The representative results of the immunohistological staining are shown in FIG. 7. In FIG. 7, arrowheads are added to each positively stained site shown in brown for the purpose of increasing the visibility.

Tissue-resident M2-like macrophages are cells that have been reported as cells performing the maintenance of adipocytes and adipose tissue (Satoh T. et al., Nature, 495, 524-528, 2013). An increase in these cells is considered to indicate that the maintenance of adipocytes has been activated. In addition, PPARγ is abundantly expressed in adipocyte precursor cells and indicates that immature adipocytes are produced. Therefore, an increase in PPARγ-positive adipocytes and an increase in tissue-resident M2-like macrophages mean that adipocyte rejuvenation and maintenance thereof have been activated, which suggests tissue rejuvenation (tissue regeneration).

Surprisingly, an increase in tissue-resident M2-like macrophages and an increase in PPARγ-positive adipocytes were also observed on the untreated side, later than the increase on the treated side. For example, the bottom panels of FIG. 7 are the results of the immunohistological staining of the untreated side (right half of the head). In the bottom panels of FIG. 7, an increase in tissue-resident M2-like macrophages and an increase in PPARγ-positive adipocytes were observed compared to the right half of the head before the treatment, showing that the effect of the treatment propagated to the region that was not treated. Moreover, although the increase was observed also in sites away from the treated side, the increase occurred later as it was further away. It was suggested that the ameliorating effect on the scalp was initiated at the treated site, and that this propagated to the surroundings, leading to an ameliorating effect of the surrounding scalp.

Example 9: Relationship Between the Amelioration of the Scalp and the Ameliorating Effect on Hair Quality In the above Example 1, although a change over time in the number of hairs was visually observed, no significant effect was detected. According to the above Examples 2 to 7, it became clear that the regeneration and modification of the scalp and the skin occurred in the ASC-CM 0.4 µg administration group, and that this had the effect of increasing the hair quality.

In the present Example, from the results of the above Examples, the treatment effect in the ASC-CM 0.4 µg administration group was assessed, focusing on fast-growing hair. Specifically, hair growing 0.9 mm or more in 3 days was extracted from the scalp image, and the total sum of the lengths of growth was calculated. Adult hair is known to grow at a rate of about 10 mm per month (that is, a rate of about 1 mm in 3 days).

Figure 8A:
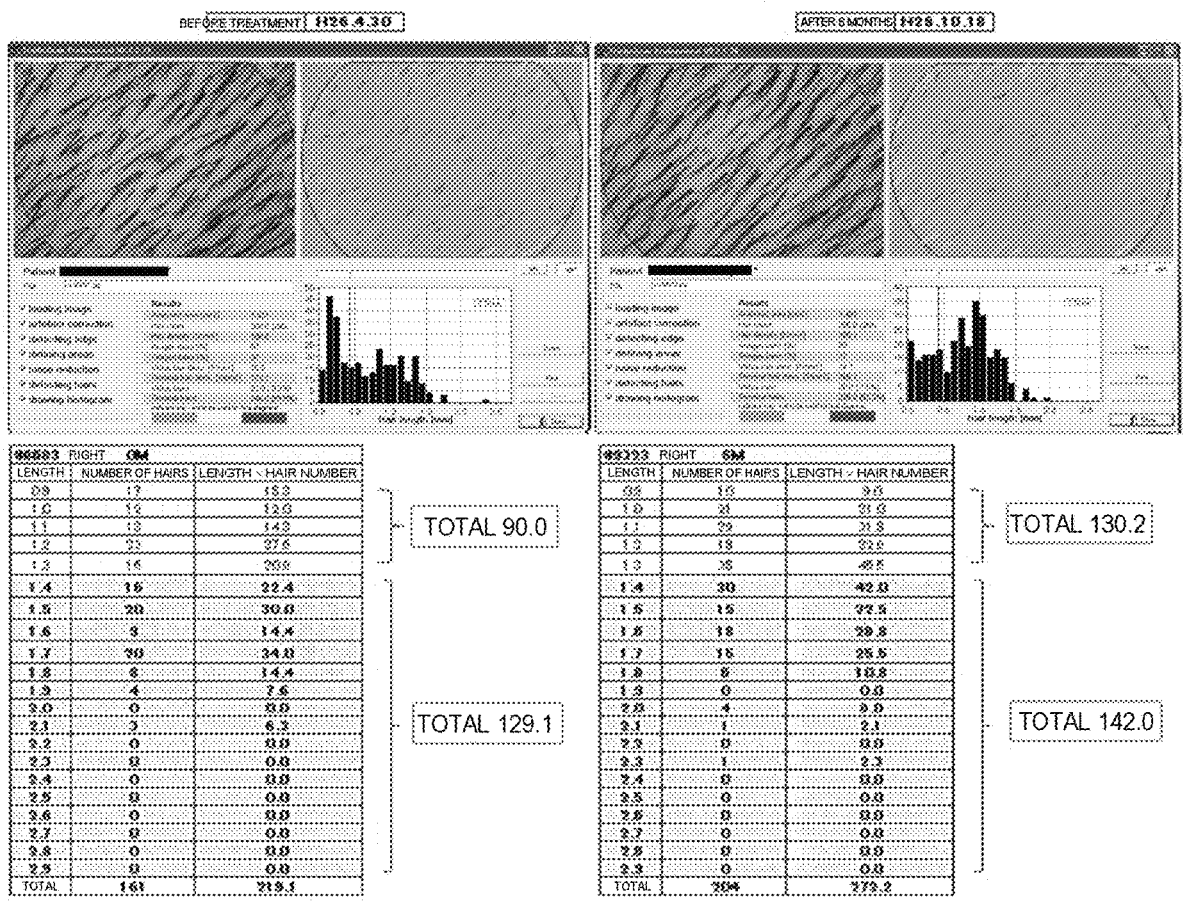
FIG. 8A shows the growth rate of hair and the total sum of the growth rate in the ASC-CM 0.4 μg administration group.

For this purpose, a portion of the scalp of a plurality of adults who were administered 0.4 µg/site of ASC-CM five times (administered once a month) was shaved and an image of the shaved site was taken three days later to perform image analysis. After shaving, the hair had a length of 0.4 mm on average. Below, the total sum of the lengths was calculated for the hair which had a length of 1.4 mm or more three days after shaving. The measurements were performed on 3 patients (patients A to C). The count results for patient C is shown in FIG. 8A as a representative example.

Figure 8B:
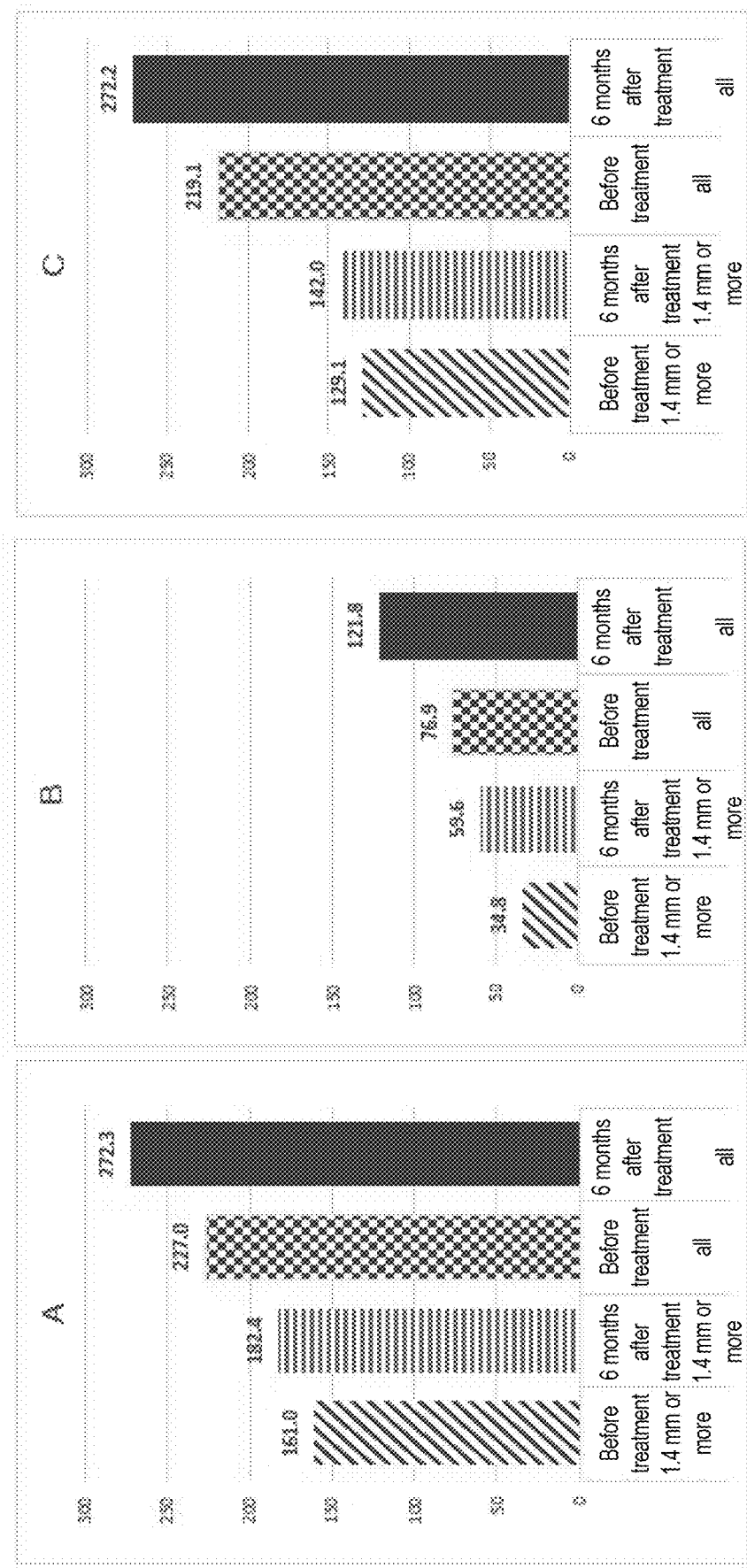
FIG. 8B is a graph showing the total sum of hair lengths before and after treatment of three patients measured by the method of the above FIG. 8A.

Moreover, the data for each of the three patients are shown in FIG. 8B. In FIG. 8B, the data before treatment and 6 months after treatment (after 6 M) are compared. In FIG. 8B, both the total sum of the lengths of hair having a length of 1.4 mm or more three days after shaving (1.4 mm or more) and the total sum of the lengths of all hair including hair less than 1.4 mm three days after shaving (all) are also shown. As shown in FIG. 8B, in patient A, the total sum of the lengths for hair having a length of 1.4 mm or more after 3 days was 161.0 before treatment and increased to 182.4 at 6 months after treatment. In patient B, the total sum of the lengths for hair having a length of 1.4 mm or more after 3 days was 34.8 before treatment and increased to 59.6 at 6 months after treatment. In patient C, the total sum of the lengths for hair having a length of 1.4 mm or more after 3 days was 129.1 before treatment and increased to 142.0 at 6 months after treatment.

As shown in FIG. 8B, the total sum of the lengths for all the hair 3 days after shaving was, in patient A, 227.0 before treatment and increased to 272.3 at 6 months after treatment. In patient B, it was 76.9 before treatment and increased to 121.8 at 6 months after treatment. In patient C, it was 219.1 before treatment and increased to 272.2 at 6 months after treatment. Thus, with the ASC-CM 0.4 µg administration, scalp modification and the resulting amelioration in the growth rate of the hair were observed. When considered together with the results of Example 1, it can be seen that the effect of the ASC-CM 0.4 µg administration was stronger on the hair growth rate than the number of hairs. Moreover, it was thought that the hair growth rate was overall lower, and the condition of the scalp was poorer in patient B compared to patients A and C. According to FIG. 8B, it is clear that the ASC-CM 0.4 µg administration exerted a modifying effect on the scalp, even on patients with such poor scalp conditions.

In addition, when examining the hair with a length of 1.4 mm or more after 3 days, it became clear from the image analysis that it was thicker compared to the hair with slow growth rate (hair with a length of less than 1.4 mm after 3 days). Specifically, the thickness of hair with a length of 2.1 to 2.2 mm 3 days after shaving was 97.42 µm on average for two patients, while the thickness of hair with a growth of less than 1.4 mm was 75.39 µm on average for the above two patients. These results show that thick hair whose growth rate was fast increases with the ASC-CM 0.4 µg administration. With the ASC-CM 0.4 µg administration, amelioration in hair tension and stiffness was observed (hair tension and stiffness increased, and an increase in hair volume was observed), but this and the increase in thick hair were consistent results.

Thus, the modification of the scalp led to the amelioration of the hair growth rate and to an increase in thick hair with tension and stiffness.

The invention claimed is:

1. A method for modifying scalp or skin in a subject in need thereof, the method comprising intradermally or subcutaneously injecting a secretion from adipose stem cells to the scalp or skin of the subject to induce adipocytes having 25 µm or less in diameter in a modified scalp or skin,
   wherein 0.3 to 0.6 µg of the secretion is injected in terms of the mass of protein contained per injection in the scalp or skin, and
   wherein the secretion is obtained by culturing adipose stem cells in a culture medium under hypoxic conditions and recovering the culture supernatant containing the secretion.

2. The method according to claim 1, wherein the secretion is injected at a rate of 1 injection per 1 $cm^2$ to 4 $cm^2$ of a surface of scalp or skin.

3. The method according to claim 1, wherein the secretion is injected in a solution volume of 10 to 30 µL per site.

4. The method according to claim 1, wherein the injection interval is from twice a month to once every 6 months.

5. The method according to claim 1, wherein the subject is a human subject.

6. A method of inducing adipocytes having 25 µm or less in diameter in a scalp or skin in a subject in need thereof, comprising intradermally or subcutaneously injecting a secretion from adipose stem cells to the scalp or skin of the subject to induce adipocytes having 25 µm or less in diameter in the scalp or skin injected with the secretion,
   wherein 0.3 to 0.6 µg of the secretion is injected in terms of the mass of protein contained per injection in the scalp or skin, and
   wherein the secretion is obtained by culturing adipose stem cells in a culture medium under hypoxic conditions and recovering the culture supernatant containing the secretion.

* * * * *